United States Patent [19]

Knute

[11] 4,397,648
[45] Aug. 9, 1983

[54] DROP SENSING UNIT AND ASSOCIATED DRIP CHAMBER FOR IV FLUID ADMINISTRATION

[75] Inventor: Wallace L. Knute, Del Mar, Calif.

[73] Assignee: Ivac Corporation, San Diego, Calif.

[21] Appl. No.: 204,771

[22] Filed: Nov. 7, 1980

[51] Int. Cl.³ .............................................. A61M 5/16
[52] U.S. Cl. .................................. 604/253; 73/861.41; 128/DIG. 13
[58] Field of Search ........... 128/214 C, 214 E, 214 Z, 128/DIG. 13; 73/861.41; 604/253

[56] References Cited

U.S. PATENT DOCUMENTS

| | | | |
|---|---|---|---|
| 3,500,366 | 3/1970 | Chesney et al. | 128/214 E X |
| 3,596,515 | 8/1971 | Cramer | 73/861.41 |
| 4,038,981 | 8/1977 | LeFevre et al. | 604/65 |
| 4,038,982 | 8/1977 | Burke et al. | 128/214 E |
| 4,321,461 | 3/1982 | Walter et al. | 128/214 E X |
| 4,346,606 | 8/1982 | Cannon et al. | 73/861.41 |

Primary Examiner—Dalton L. Truluck
Attorney, Agent, or Firm—Fulwider, Patton, Rieber, Lee & Utecht

[57] ABSTRACT

A drop sensing unit and associated, disposable drip chamber for dedicated use with the sensing unit in an IV fluid administration system, the sensing unit being adapted for convenient installation on and removal from the drip chamber, with cooperable engaging means on the sensing unit and chamber serving to locate and retain them in the desired relative position during use. Such engaging means provide for contact between the sensing unit and chamber at vertically spaced locations for effective retention, and are constructed and arranged to aid in preventing use of the sensing unit on drip chambers which differ from the specially designed chamber.

14 Claims, 8 Drawing Figures

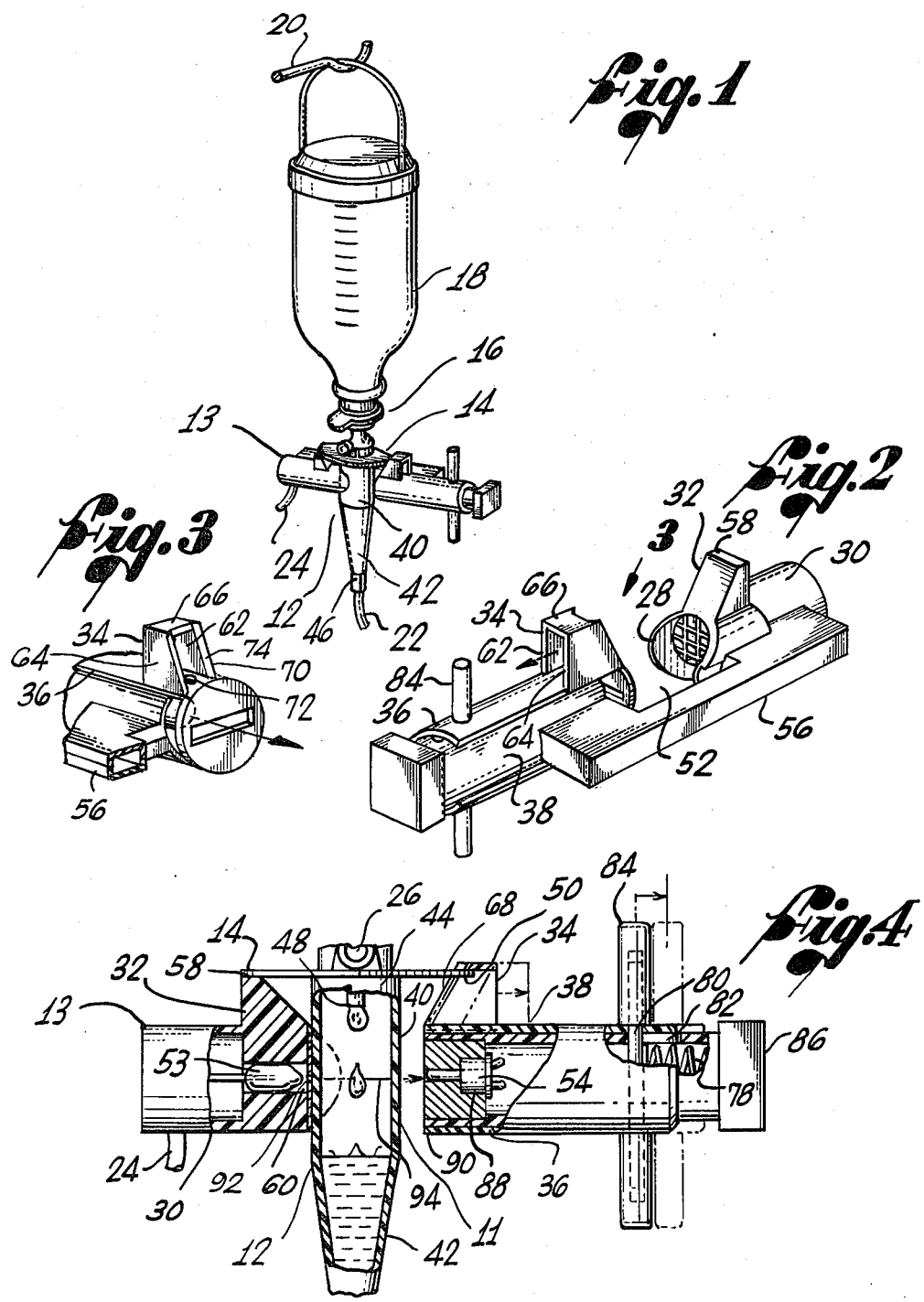

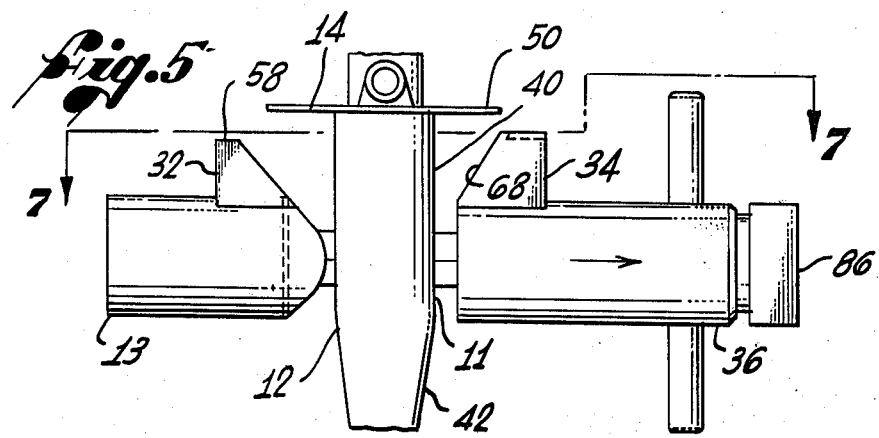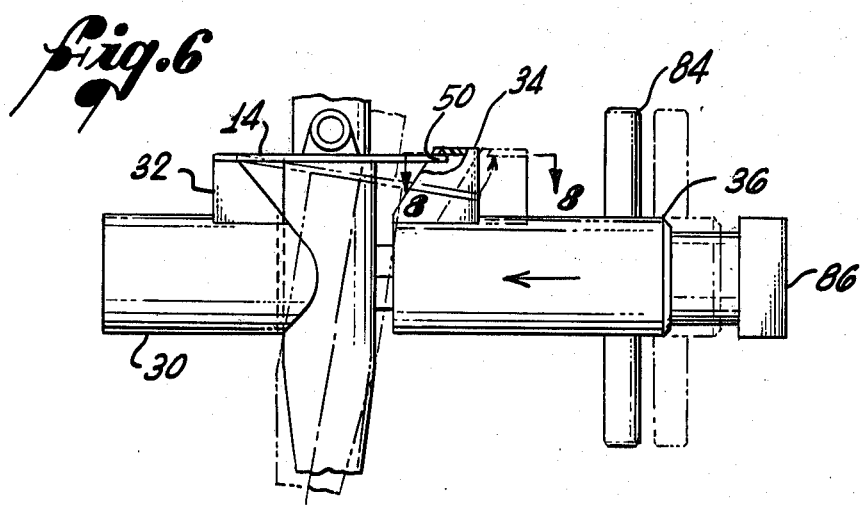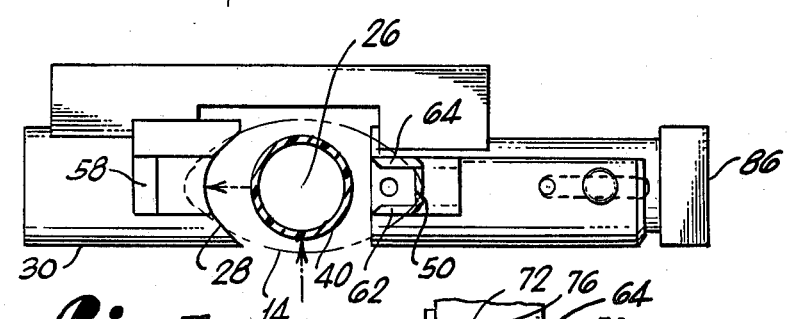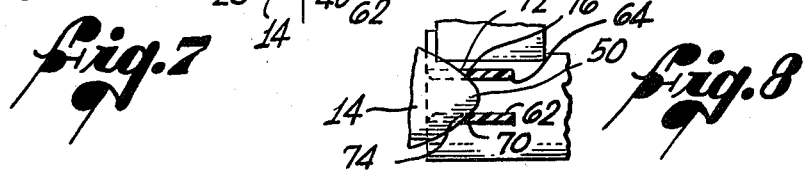

DROP SENSING UNIT AND ASSOCIATED DRIP CHAMBER FOR IV FLUID ADMINISTRATION

BACKGROUND OF THE INVENTION

This invention relates generally to parenteral fluid administration (referred to herein as "intravenous administration" or "IV administration") and, more particularly, to an improved IV drop sensing unit and dedicated or associated drip chamber for use in an IV fluid administration system whereby installation, retention and removal are enhanced and aid is afforded in preventing use of chambers with operating characteristics differing from those desired.

IV fluid administration has conventionally involved use of a disposable fluid administration set with an elongated drip chamber. Discrete fluid drops fall from a drop former to a reservoir and may be observed or detected through a transparent wall as they fall through the chamber.

Instrumentation systems for monitoring or controlling the rate of gravity flow through such administration sets, or actually pumping fluid under positive pressure through them, have made use of drop sensing units. One such unit, described in U.S. Pat. No. 3,596,515, removably clamps onto the drip chambers of a variety of sizes and shapes, and utilizes a self-contained light source and photoelectric sensor to detect drops.

Proper positioning of the sensing unit on the chamber of these prior systems so that the light beam of the sensor intercepts all falling drops is a requirement. Various expedients to aid in proper positioning have been used.

With certain types of fluid administration systems, it is especially important that only sets with certain predetermined operating characteristics be utilized. One such system provides for directly setting the desired delivery rate in milliliters per hour and, in turn, monitors the drop rate via the sensing unit and compares it with the desired rate. As is apparent, it is assumed with such a system that the drops are of a specified size, e.g., 60 drops per milliliter. Should the drop size differ, e.g., the drops be 20 drops per milliliter in size, performance clearly is adversely affected.

For accuracy considerations, it is particularly desirable with volumetric systems of the type just described that there be minimal variation in drop size from set to set. This is a matter that is subject to control in a given manufacturing operation tailored to accomplish that result.

Some prior art systems have employed sensing units with mounting elements that engage mating retention elements on a dedicated or associated set. This is for the purpose of positioning and preventing use of other than the associated set. However, these prior systems have not been entirely effective in establishing and maintaining proper positioning. Moreover, such sensing units have been inconvenient to install and remove from the drip chamber of the dedicated or associated set.

It will be appreciated from the foregoing that there has been and is a continuing need for an improved drop sensing unit and associated, dedicated drip chamber with cooperating means to aid in easily, rapidly, and reliably positioning the unit and chamber relative to one another. The sensing unit should desirably aid in preventing use on any drip chamber other than the specially designed and manufactured item. A further attribute desired is that the sensing unit be adapted for each installation and removal.

SUMMARY OF THE INVENTION

The present invention solves the need that exists and resides in an improved drop sensing unit and dedicated or associated drip chamber. Retaining means on the chamber and sensing unit provide for positive and proper positioning of the elements relative to one another in an automatic self-aligning action, yet enable the sensing unit to be conveniently installed on and removed from the chamber. Additionally, the retaining means incorporate engaging means selectively movable toward and away from one another during installation and removal. The range of movement of such engaging means is limited, and in this manner the sensing unit is adapted to aid in preventing use of drip chambers other than those of the dedicated or associated design.

The desired operating characteristics are achieved by having the engaging means at oppositely disposed and vertically spaced locations relative to the vertically oriented chamber. This arrangement is advantageous with respect to positioning and restrains the sensing unit relative to the chamber. Additionally, it facilitates the installation and removal of the sensing unit.

In a more detailed aspect of the invention, cantilevered projections adjacent the upper end of the drip chamber and cooperating latching and stabilizing posts on the sensing unit, and conforming contact surfaces on the sensing unit and chamber together comprise the engaging means. The support and stabilizing posts contact the projections as the sensing unit is spring actuated to a closed position to urge the sensing unit and chamber into the desired relative position. In the final position, the conforming surfaces on the sensing unit and wall of the chamber make contact at a location vertically spaced from the projections and restrain the drip chamber against both relative vertical and lateral movement.

The extent of actuating movement of elements of the sensing unit is limited so as to provide for positioning engagement only on one of the projections adjacent its terminal end and on the chamber at the vertically spaced location. This limit of travel excludes a clamping action being applied directly to the wall of the chamber on both sides thereof. In this manner, the sensing unit aids in preventing use of nondedicated sets.

BRIEF DESCRIPTION OF THE DRAWINGS

FIG. 1 is a perspective view of a dedicated drip chamber and sensing unit embodying the invention installed in an IV administration system.

FIG. 2 is a perspective view on an enlarged scale of the sensing unit.

FIG. 3 is an enlarged fragmentary perspective view of a portion of the sensing unit taken in the direction of the arrowed line 3 in FIG. 2.

FIG. 4 is an elevational view, with certain parts shown in longitudinal section, of the drip chamber and sensing unit in operable relation.

FIG. 5 is an elevational view of the sensing unit in the initial stage of installation on the drip chamber.

FIG. 6 is an elevational view of the sensing unit at a further stage of installation (phantom lines) and finally installed (solid lines) on the drip chamber.

FIG. 7 is an elevational view taken along the line 7—7 in FIG. 5, with certain portions being shown in section.

FIG. 8 is a fragmentary sectional view of the contact between the wing and the latch post taken along line 8—8 in FIG. 6.

DESCRIPTION OF THE PREFERRED EMBODIMENT

As shown in the drawings for purposes of illustration, and particularly in FIG. 1 thereof, the presently preferred embodiment of the invention includes a dedicated or associated disposable drip chamber 12 and a specially designed, reusable sensing unit 13 actuable for installation on or removal from the drip chamber 12. This assembly is intended for use as a component part of a solution administration system 16 wherein a bottle 18 suspended from a hook 20 feeds the dripping of fluid through the drip chamber 12 into a delivery tube 22. The electronic signals, initiated in the sensing unit 13 as each drop breaks a light beam, are transmitted to electronic signal conditioning, counting, and integrating means (not shown) through signal cable 24 to allow remote and automatic monitoring of solution administration.

In accordance with the present invention and most easily observed in FIG. 4, the drip chamber 12 is provided with a generally elliptically shaped cantilever wing 14 mounted at the upper end 44 of the drip chamber 12. The photoelectric sensing means is contained within the body of the sensing unit 13, and for proper operation the photoelectric sensing means must be mounted so that the optical path 94 is normal to the drip chamber cylindrical axis 26 at a fixed distance below the cantilever wing 14.

The first housing section 30 is provided with a conforming surface 28 (FIG. 2) having proper curvature for conforming to the lateral cylindrical surface 11 of drip chamber 12. This conforming surface 28 is vertically spaced from cantilever wing 14 along the drip chamber cylindrical axis 26. A stabilizing post 32 is mounted on the first housing section 30 so that it may be placed in contact with and rest against the underside of the cantilever wing 14. A latch post 34 presenting an inclined plane 68 to cantilever wing 14 is mounted to a sleeve 36 slidably mounted over a second housing section 38. The latch post 34 may be engaged to the cantilever wing 14 by retracting the sleeve 36 and then urging the sleeve forward by spring biasing action until contact is achieved. It is found that the contacts produced by the conforming surface 28, the stabilizing post 32 and the latch post 34 result in a stable, easily attached and detached mount. Thus, retention is achieved by a combination of engaging of two contact surfaces and the latching of the latch post 34 to cantilever wing 14.

The drip chamber 12 for delivering fluid from bottle 18 to delivery tube 22 is generally of hollow tubular form and consists of a cylindrical portion 40 joined to a lower conical portion 42 whose small end 46 is suitable for receiving delivery tube 22. Near the uper end 44 and lying substantially on the drip chamber cylindrical axis 26 of the cylindrical portion 40 is located a drop former 48. The drop former 48 is a precision hollow tube which emits drops of fluid at a precise size determined by its dimensions. The drip chamber 12 thereby serves as a precision metering device in the solution administration system 16.

To allow attachment of the sensing unit 13, the drip chamber 12 is provided with a plurality of cantilever projections oppositely disposed in pairs across a diameter of the cylindrical portion 40. In the preferred embodiment, the cantilever wing 14 defines a pair of projections firmly attached transversely to the drip chamber cylindrical axis 26 near the upper end 44 of the cylindrical portion 42. The cantilever wing 14 is substantially flat and of generally elliptical shape, preferably formed of a single piece of plastic or like material. The shape of the end portion 50 found at either elongated end of the cantilever wing 14 is suitably narrowed to mate with the latch post 34, allowing attachment of the sensing unit 13. The cantilever wing 14 is symmetrical about its shorter axis, thereby allowing the latch post 34 to be mated with either narrow end portion 50.

The sensing unit 13 generally comprises a tubular housing with a central sensing gap 52 for receiving the drip chamber 12. The tubular housing includes a first housing section 30 containing the light source 53 and a second housing section 38 containing the photocell 54 and supporting the sleeve 36. The two sections 30 and 38 are supported in fixed coaxial relation by a hollow external bridging member 56. Hollow bridging member 56 allows electrical communication between sections 30 and 38.

The first housing section 30 provides two of the contact surfaces for orienting the sensing unit 13 properly in relation to the drip chamber 12. A conforming surface 28 on the portion of the first housing section 30 adjacent the sensing gap 52 is adapted to contact the lateral cylindrical surface 11 of drip chamber 12. The stabilizing post 32 is adapted to contact and rest against the lower side of the cantilever wing 14 at the stabilizing post contact surface 58. The light source 53 is located in a first cavity 60 within the first housing section 30.

Second housing section 38 contains a second cavity 88 for receiving photocell 54. Section 38 also supports spring-biased sleeve 36. Sleeve 36 is biased toward the sensing gap 52 by spring 78 carried within the second housing section 38. The limit of movement of sleeve 36 is defined by the motion of rod 80 in slot 82. The length of bridging member 56 is chosen so that the minimum spacing along the optical path 94 between facing end 90 of sleeve 36 and facing end 92 of first housing section 30 is substantially larger than the diameter of cylindrical portion 40, so that sensing unit 13 may not be clamped directly using both facing ends 90 and 92 to the lateral cylindrical surface 11.

Rod 80 also conveniently supports a pair of finger grip rods 84 mounted radially outward from opposite sides of sleeve 36. In conjunction with the enlarged outer sealed end 86 the rods 84 form a syringe-type grip familiar to medical personnel for selectively retracting the sleeve to enable mounting or removal of sensing unit 13. Sleeve 36 carries a latch post 34 adapted for engaging the end portion 50 of cantilever wing 14. Latch post 34 includes side members 62 and 64 and a top member 66. The side members 62 and 64 define an inclined plane surface 68. The inclined edges 70 and 72 of the side members 62 and 64 have bevel surfaces 74 and 76 to generally conform to the curvature of the end portion 50 (FIG. 8) thereby promoting a camming action of movement of end portion 50 into proper contact with top member 66 during attachment procedures.

Attachment of sensing unit 13 to drip chamber 12 is accomplished as shown in the sequence FIG. 5, FIG. 6 and FIG. 4. Sleeve 36 is first retracted by compressing spring 78 through opposing pressure on rods 84 and sealed end 86. Sensing unit 13 is moved into its approximate position with drip chamber 12 lying generally within sensing gap 52. This approximate positioning may be accomplished by moving sensing unit 13 generally along a radius of cylindrical portion 40 rather than parallel to the drip chamber cylindrical axis 26. This ability to introduce the sensing unit 13 from the side using only a single hand rather than from below represents a significant convenience feature for hospital personnel.

During a normal attachement procedure after the approximate positioning of sensing unit 13 but before spring 78 is released, there may be some misorientation between the sensing unit 13 and drip chamber 12, as shown in FIG. 6. Final positioning is achieved by first moving sensing unit 13 in a generally axial direction upward until stabilizing post 32 contacts the underside of cantilever wing 14. The end portion 50 then will have contacted side members 62 and 64 and will rest in a symmetrical position between inclined edges 70 and 72 as a result of the action of the bevel surfaces 74 and 76.

Upon gradual releasing of tension in spring 78, end portion 50 will be spring biased into position for engaging latch post 34 by a cam action along inclined edges 70 and 72. The drip chamber 12 is urged into its proper aligned position with the self-aligning action produced by movement of sleeve 36. As sleeve 36 reaches its point of furthest travel toward section 30, the lateral cylindrical surface 11 of drip chamber 12 achieves full contact with conforming surface 28, stabilizing post 32 contacts the underside of cantilever wing 14 along contact surface 58 and end portion 50 completes engagement of latch post 34 by contacting the lower side of top member 66. Sensing unit 13 is then securely but removably held to drip chamber 12 so that optical path 94 is substantially normal to the cylindrical axis 26 and at a fixed axial location.

By virtue of the engagement cooperation between latch post 34 and cantilever wing 14 and the limitation on the extent of the closing movement of sleeve 36 by rod 80 is slot 82, sensing unit 13 cannot be directly clamped on a drip chamber having no cantilever wing 14 or functional equivalent. If an attempt is made to mount sensing unit 13 on such an improper drip chamber, the loose fit will result in sensing unit 13 falling away from the drip chamber of otherwise indicating the error to an attendant, thereby aiding in preventing use of an improper set.

It will now be appreciated that, through use of this invention, a sensing unit may be securely mounted to a drip chamber in the proper operating position easily and securely using only one hand. Additionally, the cooperating arrangement of projections on the drip chamber and the described latching mechanism on the drop sensor aid in preventing use of the drop sensor with any drip chamber for which it is not specifically designed. Although a particular embodiment of the invention has been described in detail for purposes of illustration, various modifications may be made without departing from the spirit and scope of the invention. Accordingly, the invention is not to be limited except as by the appended claims.

I claim:

1. Apparatus for producing and monitoring drop flow, comprising:
    a drop sensing unit;
    an associated drip chamber having mounting means thereon;
    first means on said drop sensing unit supportively and removably engaging said mounting means of said drip chamber and including alignment means automatically positioning said drip chamber relative to said drop sensing unit while simultaneously restraining said drop chamber against lateral or vertical movement relative to the vertical path of normal drop flow through the chamber, said first means and said mounting means cooperating to restrict said drop sensing unit to use with said associated drip chamber to provide accurate drop flow monitoring; and
    second means on said drop sensing unit engaging said drip chamber at least at a location vertically spaced from said mounting means along said path, said second means cooperating with said supportively engaging first means to exert clamping forces on said drip chamber substantially normal to said path at no more than three regions of engagement.

2. Apparatus as set forth in claim 1, wherein said alignment means includes a camming surface adapted to engage said drip chamber mounting means.

3. Apparatus as set forth in claim 2, further including biasing means on said drop sensing unit urging said first means into engagement with said mounting means.

4. In an IV fluid monitoring system including a sensor housing and an associated elongated drip chamber, a system of supporting and aligning the associated drip chamber relative to a sensing path defined by the drop sensor housing, comprising:
    means supportively and removably engaging the drip chamber with the drop sensor housing at a plurality of vertically spaced-apart contact areas along the longitudinal axis of the drip chamber and on opposite sides thereof; and
    camming means on the drop sensor housing removably engaging cooperable means located on only one side of the drip chamber to position the longitudinal axis of the drip chamber normal to the sensing path defined by the drop sensor housing and simultaneously to bias the drip chamber against misalignment with the drop sensor housing, said camming means further providing a limit to vertical movement of the drip chamber relative to the drop sensor housing in one direction only during installation of the drop sensor to the drip chamber.

5. For use with an associated drip chamber having an elongated and generally vertically oriented body with a plurality of cantilevered projections extending laterally therefrom, a drop sensing unit comprising:
    drop sensing means;
    a support housing for said drop sensing means defining a contoured engagement surface adapted to engage said chamber body at a location vertically spaced from said projections;
    latch means connected to said support housing with a cam surface thereon engageable with one of said projections and arranged for movement toward and away from said contoured surface, said latch means being adapted to urge said chamber into a captured state relative to said support housing; and
    resilient means urging said latch means toward said contoured surface.

6. The sensing unit of claim 5 wherein said latch means is limited in its movement toward said contoured surface to a distance less than the lateral spacing between the distal ends of said projections but greater than the maximum lateral width of said body.

7. Apparatus for producing and monitoring drop flow, comprising:

a drop sensing unit;

an associated drip chamber including mounting means;

first means on said drop sensing unit supportively and removably engaging only said mounting means and including aligning means for automatically positioning said drip chamber relative to said drop sensing unit for accurate drop flow monitoring while simultaneously restraining said drip chamber against movement relative to the vertical path of normal drop flow through said chamber; and second means removably engaging said drip chamber on only an opposite side of said drip chamber from said first means, said second means cooperating with said supportively engaging first means to exert a clamping force substantially normal to said path of drop flow, said clamping force being exerted at three regions of engagement, said first and second means being vertically spaced apart along said path and being laterally spaced apart sufficiently to be incapable of exerting a clamping force on only said drip chamber.

8. Apparatus as set forth in claim 7, wherein said aligning means includes a cam surface on said first means.

9. Apparatus as set forth in claim 8, wherein said first means comprises latching means movably mounted on said drop sensing unit, and wherein said second means comprises at least one contact surface on said drop sensing unit.

10. Apparatus as set forth in claim 9, wherein said second means comprises two vertically spaced contact surfaces on said drop sensing unit.

11. Apparatus for producing and sensing a succession of discrete fluid drops in an intravenous fluid administration system, comprising:

a drop sensing unit;

an associated drip chamber having an elongated and generally vertically oriented body and integrated drop forming means, said drop sensing unit being removably mounted on said chamber and including a housing;

sensing means on said housing;

retaining means positioning and holding said drop sensing unit in relation to said chamber with said sensing means in operable relation to the path of drops from said drop forming means, said retaining means having cooperable engaging means on said chamber and on said drop sensing unit that contact one another at vertically spaced and generally oppositely disposed locations, said engaging means including a first projection extending laterally from said elongated body, a latch post on said housing engageable with said projection, and conforming contact surfaces on said housing and said body, with the location of said contact surfaces being vertically spaced from the location of engagement of said projection with said latch post; and actuating means on said housing selectively operable to move said latch post toward and away from engagement with said first projection to exert a clamping force on said drip chamber body at vertically spaced locations to effect installation, retention, and removal of said sensing unit relative to said associated drip chamber.

12. The apparatus of claim 11 wherein said engaging means further includes:

a second projection extending laterally from said elongated body in a direction generally opposite that of said first projection; and a stabilizing post on said housing engageable in supporting contact with at least a portion of said second projection.

13. The apparatus of claim 11 wherein said drip chamber body has oppositely disposed and laterally extending projections; and wherein said latch post means further includes a cam surface engageable with one of said projections during mounting of said sensor unit on said drip chamber and, thereafter, capturing said one of said projections, whereby said sensing unit and drip chamber are urged into and maintained in the desired relative position for use.

14. The apparatus of claim 13 wherein said projections are formed as a wing of generally elliptical configuration, with two relatively narrow ends oppositely disposed at each end of the major axis of such wing, said ends being adapted to conform to and engage with said latch post means.

* * * * *